United States Patent
Maunder

(10) Patent No.: US 9,115,836 B2
(45) Date of Patent: Aug. 25, 2015

(54) TUBE RETAINER

(75) Inventor: Roy Peter Maunder, Lovedean (GB)

(73) Assignee: BioPure Technology Limited, Parklands Business Park, Denmead, Hampshire (GB)

( * ) Notice: Subject to any disclaimer, the term of this patent is extended or adjusted under 35 U.S.C. 154(b) by 250 days.

(21) Appl. No.: 12/907,627

(22) Filed: Oct. 19, 2010

(65) Prior Publication Data

US 2011/0089683 A1 Apr. 21, 2011

(30) Foreign Application Priority Data

Oct. 20, 2009 (GB) .................................. 0918442.5

(51) Int. Cl.
*F16L 33/22* (2006.01)

(52) U.S. Cl.
CPC .................................... *F16L 33/225* (2013.01)

(58) Field of Classification Search
CPC .................................................... F16L 33/225
USPC .................................. 285/243, 257, 242, 259
See application file for complete search history.

(56) References Cited

U.S. PATENT DOCUMENTS

| | | | | |
|---|---|---|---|---|
| 1,098,294 A | * | 5/1914 | Patty | 285/249 |
| 1,532,886 A | * | 4/1925 | Cowles | 285/243 |
| 2,420,617 A | * | 5/1947 | Paquin | 285/243 |
| 2,470,538 A | * | 5/1949 | Wolfram et al. | 285/249 |
| 2,868,564 A | * | 1/1959 | Arras | 285/243 |
| 3,083,989 A | * | 4/1963 | Press | 285/110 |
| 3,724,882 A | * | 4/1973 | Dehar | 285/243 |
| 4,257,629 A | * | 3/1981 | Maple et al. | 285/12 |
| 4,946,200 A | * | 8/1990 | Blenkush et al. | 285/38 |
| 6,089,621 A | * | 7/2000 | Nishio | 285/331 |
| 7,118,136 B2 | * | 10/2006 | Ohya | 285/3 |
| 2003/0193190 A1 | * | 10/2003 | Werth | 285/243 |
| 2004/0217589 A1 | * | 11/2004 | Mittersteiner et al. | 285/255 |
| 2005/0189765 A1 | * | 9/2005 | Maunder et al. | 285/305 |

FOREIGN PATENT DOCUMENTS

| | | | | |
|---|---|---|---|---|
| DE | 3525502 A1 | * | 1/1987 | F16L 37/02 |
| FR | 2806148 A1 | * | 9/2001 | F16L 33/207 |
| GB | 2274891 A | * | 8/1994 | F16L 21/08 |

* cited by examiner

*Primary Examiner* — James Hewitt
(74) *Attorney, Agent, or Firm* — Lambert & Associates; Gary E. Lambert; David J. Connaughton, Jr.

(57) ABSTRACT

A retaining clamp for retaining a tube on a barbed connector. The clamp includes a collet, having a first portion sized to fit over a tube on a barbed connector, and a plurality of fingers extending from the first portion for fitting behind the barb of a connector, the fingers having inward extensions at their distal ends for urging the tube against the connector behind the barb. The clamp also includes a sleeve, sized to fit over the collet and to urge the fingers on the collet inwards to retain the tube on the connector. The collet and sleeve are held in position with a ratchet. In addition, one of the sleeve or the collet includes an inward projection for urging the tube against the end of the barb on the barbed connector in use.

14 Claims, 5 Drawing Sheets

TUBE RETAINER

CROSS REFERENCE TO RELATED APPLICATION

This application claims the benefit of and takes priority under 35 U.S.C. §119 to United Kingdom Patent Application Number 0918442.5 filed on Oct. 20, 2009.

BACKGROUND OF THE INVENTION

1. Field of the Invention

The present invention relates to a retainer for securing a flexible tube to a barbed fitting, particularly though not exclusively for use in bio-disposable systems used in the pharmaceutical industry.

2. Description of the Related Prior Art

Fluid connections in the food, medical and pharmaceutical industries are commonly made with flanged connectors clamped to each other. The connectors have hollow spigots to which tube is connected. The flanged connectors can be made to tight tolerances, as can seals between two flanges, whereby there is little scope for stagnant accumulation at the flanges per se of material which can become contaminated, for instance by bacterial, and hence cause a problem.

However, the connection between the hollow spigot and the tubing can provide a stagnant region and thus a potential hazard. In addition, fluid leaking between the connections is lost to the process, and when using valuable fluids this can be a significant loss to the process. This arises because the nose of the connectors' spigot is tapered where it meets the tube. The latter is close to its free diameter at the small diameter end of the spigot and there is little resistance to pressurised fluid permeating between the spigot and the tube. The pressure of the fluid is liable to force the fluid right up the taper and cause a leak or at least leave a residue of fluid between the tube and the taper, and even behind the taper.

In order to minimise leakage and prevent the flexible tube from slipping off the barbed fitting tube retainers have been used. Originally, when the fittings were of metal, the retainers were jubilee clips tightened around the fitting behind the barb. When plastics material fittings came into use, cable ties became the standard method of retaining the tube on the fitting; occasionally two cable ties would be used for added security. However, while these minimise the risk of the tube being removed from the fitting, they do not prevent fluid being forced up the taper and behind the barb.

Recently the BARBLOCK® retainer has been introduced in which a collet, including a compression ring is held in position on or behind the barb with a sleeve, which locks over the collet. This again urges the tube against the fitting at a position distant from the end of the taper, and thus it is still possible for fluid to travel between the taper and the tube to the restriction point.

SUMMARY OF THE INVENTION

The object of the present invention is to provide an improved retainer.

According to the invention there is provided a retaining clamp for retaining a tube on a barbed connector, the clamp comprising:

a collet, the collet including a first portion sized to fit over a tube on a barbed connector, and a plurality of fingers extending from the first portion for fitting behind the barb of a connector, the fingers having inward extensions at substantially their distal ends for urging the tube against the connector behind the barb;

a sleeve, sized to fit over the collet and to urge the fingers on the collet inwards to retain the tube on the connector, means on the collet and/or the sleeve to secure the collet and sleeve together in use; and one of the sleeve or the collet including an inward projection for urging the tube against the end of the barb on the barbed connector in use.

In use the collet is fitted over the tube on the barb fitting with the fingers positioned behind the barb. The sleeve is then fed along the tube and urged over the collet, with a hook on one of the collet or the sleeve mating with the ratchet points on the other of the sleeve or collet, the sleeve urging the projections on the fingers against the tube behind the barb, preventing forward movement of the retainer. The sleeve is urged over the collet until the internal inward projection abuts the pointed end of the taper of the barb, preventing fluid seeping up the joint between the tube and the fitting.

The inward projection may be provided on either the sleeve or the collet and may be provided as a thickening in the wall, or as a return.

Preferably the means for securing the sleeve to the collet will be ratchet means comprising a series of projections on one of the sleeve or the collet and a hook for securing to the projections on the other of the sleeve or collet. Typically the series of projections will be provided on the collet, and in particular on the fingers of the collet, and the hook on the sleeve. However, alternatively the hook could be provided on the collet with the series of projections provided on the sleeve. This arrangement provides a degree of freedom in the distance between the inward projection and finger projections in use, to allow for different lengths of barb on the connector.

Preferably four or more fingers will be provided on the collet.

Conveniently the collet and the sleeve may be held together prior to use by frangible connections, retaining projections, or other retaining means. This enables both elements of the retainer to be slid onto the tube together. Where frangible connections are used, the collet can be pushed over the barbed connector once it has been positioned in the tube, and urging of the sleeve into position over the collet breaks the frangible connections and secures the device in place. Where retaining projections are provided, these can be designed such that the sleeve cannot be removed from the collet without passing over the fingers. Thus in use the device can be positioned on a tube, then pushed over the tube on a barbed connector, the sleeve then being pushed over the fingers of the collet to secure the device in position.

Typically the retainer will be made from polypropylene, but may also be made from any other plastics materials.

BRIEF DESCRIPTION OF THE DRAWINGS

To help understanding of the invention, a specific embodiment thereof will now be described by way of example and with reference to the accompanying drawings, in which:

FIG. 6 is a cross sectional view of the collet and sleeve according to a second embodiment of the invention; and.

DETAILED DESCRIPTION OF THE PREFERRED EMBODIMENT

Figure 1:
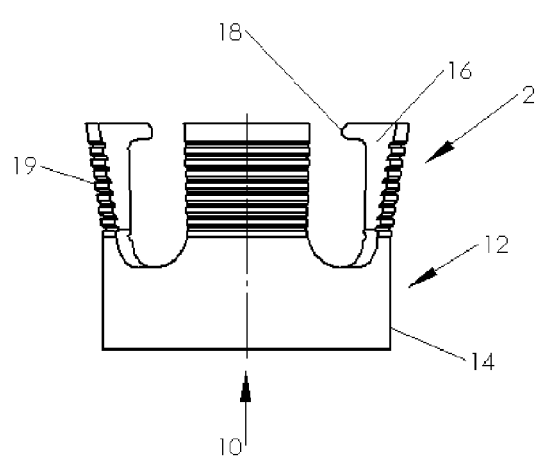
FIG. 1 is a side view of a collet of the connector of the present invention.
Figure 2:
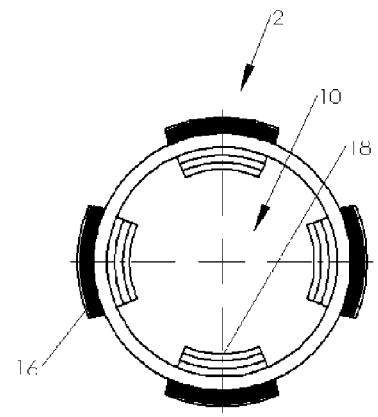
FIG. 2 is an end view of the collet of FIG. 1.
Figure 3:
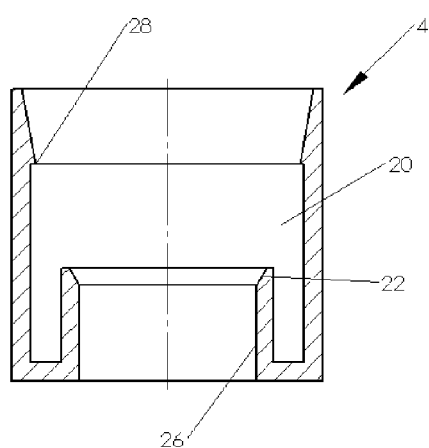
FIG. 3 is a cross-sectional view of a sleeve of a connector of the present invention.
Figure 4:
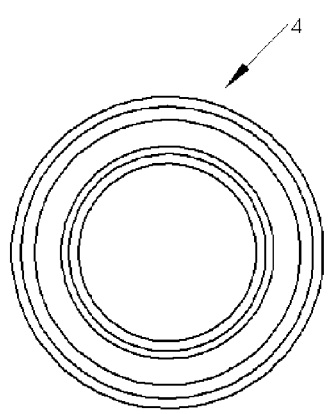
FIG. 4 is an end view of the sleeve of FIG. 3.

Referring to FIGS. 1 to 5, the retainer 1 comprises a collet 2 and a sleeve 4, designed such that in use the collet 2 fits over a tube 6 connected to a barbed connector 8, and the sleeve 4 fits over the collet, securing the same in position.

Referring to FIGS. 5 and 7-10, the spigot connector 8 can be seen having a barb 32 on it. The barb 32 can be seen to have a major dimension greater than that of the spigot 8, and has a reduced diameter distal end at its leading end. The tube 6 can be seen retained on the connector's barb 32 and spigot 8. At a first outer diameter, the tube 6 is positioned over the spigot 8 and has a diameter substantially equal to a diameter of the spigot 8, plus twice the wall thickness of the tube 6. At a second outer diameter, the tube 6 is positioned over the barb 32 major dimension and has a diameter substantially equal to a diameter of the barb 32 major dimension and twice the wall thickness of the tube 6. At a third outer diameter, the tube 6 is positioned over the reduced diameter distal end of the barb 36, and has a diameter substantially equal to a diameter of the reduced diameter distal end plus twice the wall thickness of the tube 6.

The collet 2 is essentially cylindrical with a through aperture 10 to allow it to be fed over the tube 6. At one end 12 the collet has an annular ring 14. Extending from the ring is a plurality of fingers 16 extending round the ring. In the embodiment of FIGS. 1 to 5 four fingers are shown, but any number of two or more fingers could be provided. Each finger 16 is provided with an inward projection 18 at its distal end, designed in use to fit behind the barb of the barbed connector 8. The outside of each finger is provided with a series of projections 19, or teeth, designed in use to connect with a projection on the sleeve, as will be described later.

Figure 8:
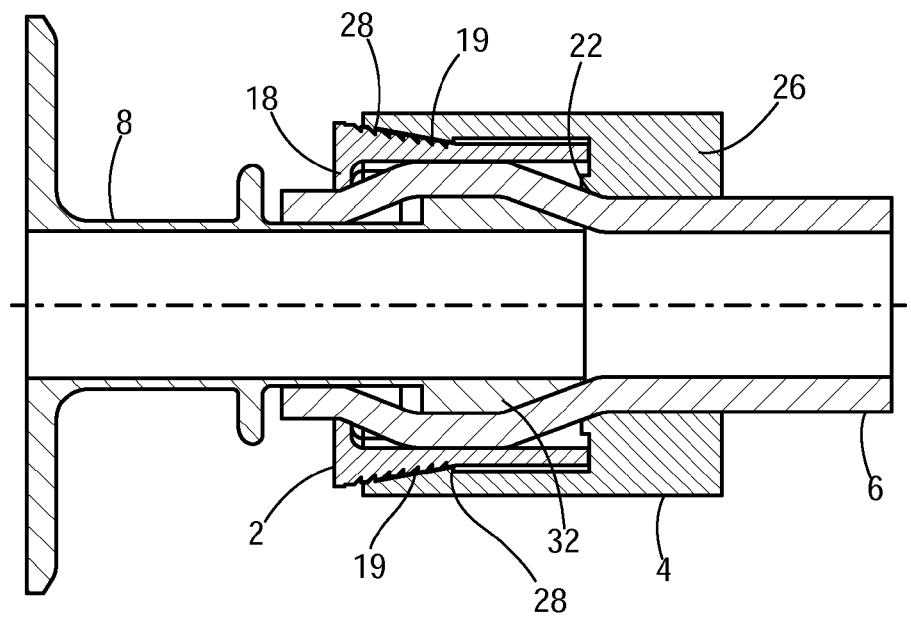
FIG. 8 is a cross sectional view of an embodiment of the collet and sleeve wherein the sloping inward projection is shown as a thickening of a wall of the sleeve.

The sleeve 4 is also essentially cylindrical in shape, sized to fit over the collet 2 and hold the same in position. The inside 20 of the sleeve is provided with an inwardly tapered surface 22, extending downwardly towards one end 24. As shown the inwardly tapered surface 22 is provided on a return 26 of the cylinder wall of the sleeve. However, the inwardly tapered surface 22 could also be provided as a thickening of the wall of the cylinder as shown in FIG. 8, or in any other manner. It has been found that a slope on the inward projection of approximately 45° is preferred as gives this the abutment with the barbed connector 8, although any angle of slope between 25° and 85° could be used. The slope is designed in use to urge the tube against the end of the barbed connector over which it is fitted.

Figure 9:
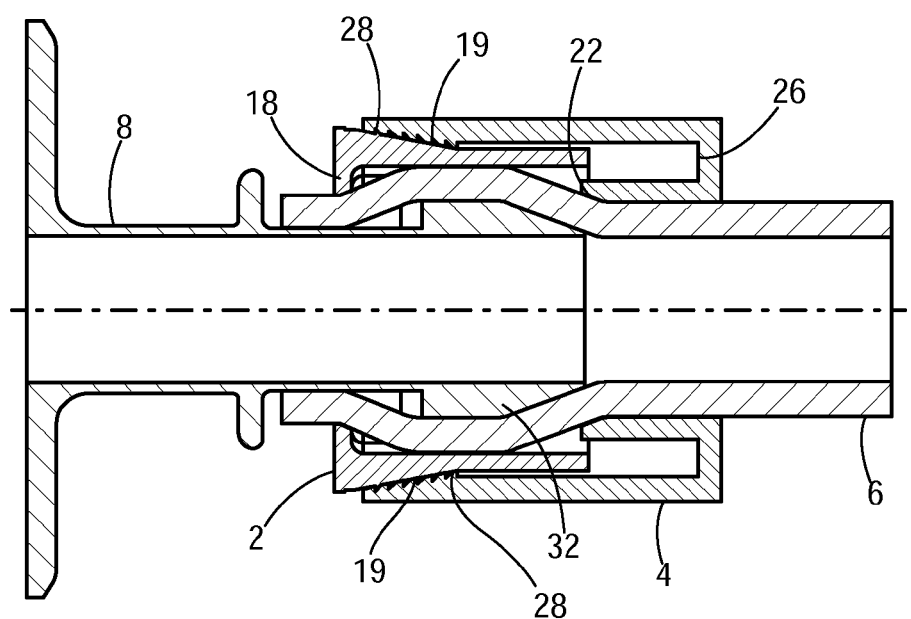
FIG. 9 is a cross sectional view of an embodiment of the collet and sleeve wherein the hook or the projection is provided on the collet with the series of projections provided on the sleeve.
Figure 10:
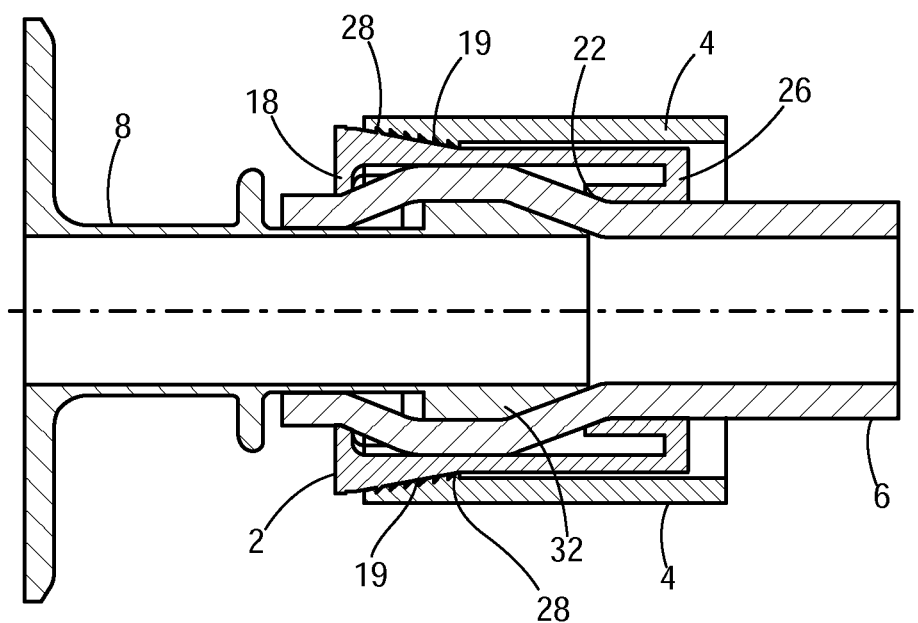
FIG. 10 is a cross sectional view of an embodiment of the collet and sleeve wherein the sloping inward projection is provided on a return on the collet.

The other end of the sleeve 4 is provided with a hook or an inward projection 28 configured to engage with the projections 19 on the collet 2, and lock the collet and sleeve together, urging the fingers of the collet inwards and together. Typically the series of projections 19 will be provided on the collet 2, and in particular on the fingers of the collet, and the hook or the inward projection 28 on the sleeve. However, alternatively the hook or the inward projection 28 could be provided on the collet 2 with the series of projections provided on the sleeve 4 as shown in FIG. 9.

For use, a flexible tube 6 is provided on to which is fed a sleeve 4, the end with the return being pushed over the end of the tube first. The collet 2 is then fed onto the tube, with the annular ring 14 being pushed over the tube first. A barbed connector is then pushed into the end of the tube 6.

Figure 5:
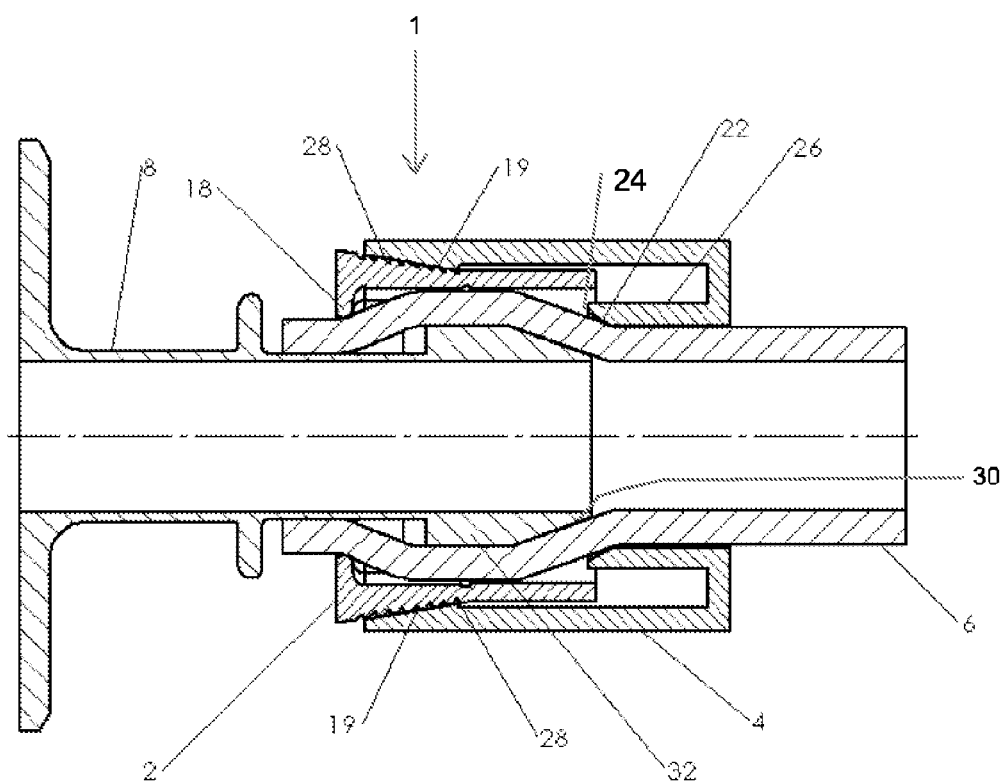
FIG. 5 is a cross-sectional view of the connector in use, connecting a flexible tube with a barbed connector

Referring now to FIG. 5, in use the collet 2 is then pushed up over the flexible tube 6, which is positioned over the barbed end of a connector 8. The collet is positioned with the annular ring 14 at the pointed end 30 of the barb 32, and the inward projections 18 of the fingers 16, behind the barb 32. The sleeve 4 is then pushed along the tube 6, and urged into position over the collet 2.

At a certain point, as the sleeve 4 is urged over the collet 6, the projection 28 on the sleeve connects with one of the series of projections 19 on the collet. As the sleeve extends further over the collet, the projection 28 on the sleeve 4 slides over the projections on the collet, engaging with the next projection, in a ratchet-like manner.

The sleeve 4 is positioned correctly once the inwardly tapered surface 22 abuts the pointed end 30 of the barb 32, through the flexible tube 6. This prevents the ingress of fluid beyond the end of the barbed connector 8. In addition, the retainer 1 is locked into position with the finger projections 18 behind the barb 32, preventing movement of the retainer 1 in one direction and the inwardly tapered surface 22 abutting the pointed end of the barb 32 preventing movement in the other direction. The sleeve and connector being locked together by the ratchet projections 19 and 28, the retainer 1 is fixed in position.

Figure 6:
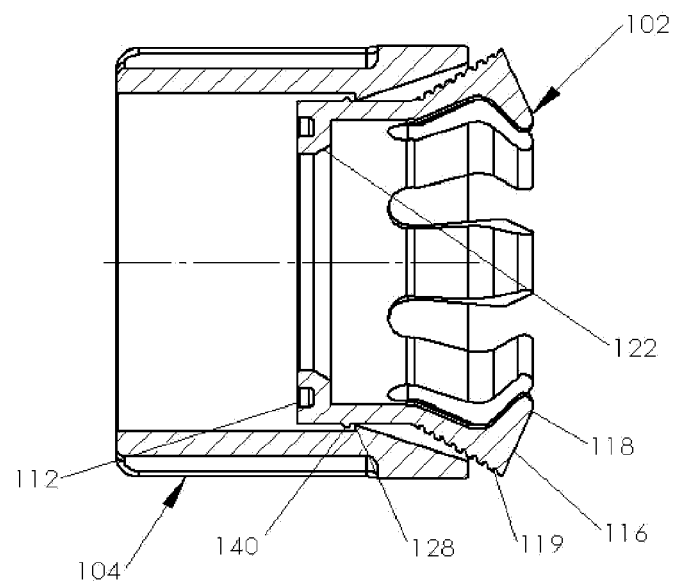
Figure 7:
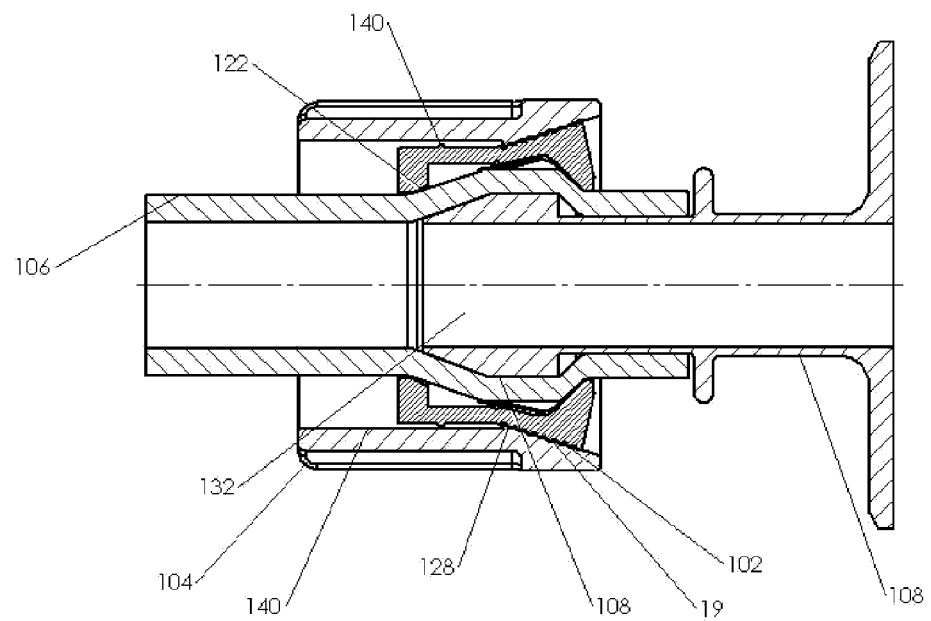
FIG. 7 is a cross-sectional view of the retaining clamp of FIG. 6 in use.

Referring now to FIGS. 6 and 7, a second embodiment of the invention will now be described, which is similar to the first with the main exception that the slope is provided on the collet.

The collet 102 comprises an annular ring 112 sized to fit over a tube on a barbed connector. Extending from one end of the collet 102 is a plurality of fingers 116. The fingers are generally flared toward their distal end, each finger 116 having a inward projection 118, with the flaring sufficient to enable tube 106 to pass between the inward projections 118. The inward projections are designed to fit behind the barb of the barbed connector 108 in use, to urge the tube against the connector 108. As shown the ends of the projections are rounded to prevent damage to the tube, while preventing the tube from being removed from the connector. Typically four, six or eight fingers will be provided, however any number may be provided.

The outside of each finger 116 is provided with a series of teeth 119 for connection with the sleeve.

The end of the collet away from the fingers 116, is shaped to provide an inwardly tapered surface 122 for abutting the end of barbed connector 132, through the tube. The inwardly tapered surface is provided at approximately 30° angle, however any other angle can be used, as discussed above.

The sleeve 104 of this embodiment is essentially cylindrical in shape. An inward facing projection or barb 128 is provided on the sleeve, to mate with the teeth 119 on the collet 102 and to lock the sleeve and collet together. In addition, the end of the sleeve past the projection is flared 126 to accommodate the flared end of the fingers.

The collet 102 and the sleeve 104 may be provided as a single unit for ease of use, with the flared end of the sleeve 104 attached to the annular ring of the collet 102 by frangible connections (not shown). While frangible connections will provide the two piece device as single unit prior to use, the breaking of the frangible connections for use can lead to the distribution of small particles of plastics material, which could lead to contamination. Thus frangible connections are not preferred.

As shown in FIG. 6, an additional projection 140 is provided on the outside of the annular ring 112 of the collet 102. This can be used to hold the collet and sleeve together; the barb 128 on the sleeve 104 preventing the sleeve from slipping over the annular ring 112 portion of the collet, and the flared fingers 116, preventing the sleeve from slipping over the finger portion of the collet. While not connecting the sleeve and the collect, they are held together prior to use to make fitting of the elements easier.

In use, as shown in FIG. 7, the unit is pushed over a tube 106 with the collet 102 towards the open end of the tube, the tube then being pushed over the barbed end of a connector 108. The collet 102 can then be moved into place with the projections 118 on the fingers 116 being position behind the barb of the connector. Pushing of the sleeve 104 over the collet is not prevented by the barb 140, and allows the sleeve to move over the collet, urging the flared fingers to gather behind the barb 132, preventing removal of the tube 106 from the barbed connector 108. The barb 128 engages with the teeth 119 and the sleeve is pushed upwards with the barb 128 ratcheting along the teeth 119. The sleeve is urged over the collet, until the inwardly tapered surface 122 of the collet 102 abuts the tube at the end of the barb on the connector, urging the tube against the barb and preventing fluid passing between the tube and the barb, causing a leak or a stagnant area.

The size and dimensions of barbed connectors vary depending upon the manufacturer. The ratchet system 128, 119 provides a degree of flexibility so that a retainer made to a standard size can fit over several different barbed connectors. However, retainers can be made to fit specific barbed connectors. A degree of flexibility should also be provided even on retainers for specific barbed connectors to allow for tolerances in manufacture and changes of temperature.

The invention is not intended to be restricted to the details of the above-described embodiment. For instance, the connector can be sized to fit any size of tube and barbed connection.

What is claimed is:

1. A retaining clamp assembly comprising:
   a tube;
   a connector; and
   a retaining clamp for retaining the tube on the connector, wherein the connector comprises:
   a spigot; and
   a barb on the spigot, the barb having:
      a barb major dimension having a diameter greater than that of the spigot; and
      a reduced diameter distal end at a leading end of the spigot;
   the tube where retained on the connector having:
      a first outer diameter at the spigot behind the barb substantially equal to a diameter of the spigot plus twice a wall thickness of the tube;
   a second outer diameter at the barb substantially equal to the diameter of the barb major dimension of the barb plus twice the wall thickness of the tube; and
   a third outer diameter at the reduced diameter distal end of the barb substantially equal to a diameter of the reduced diameter distal end of the barb plus twice the wall thickness of the tube;
   the clamp comprising:
      a collet, the collet including a first portion sized to fit over the tube on the barbed connector, and a plurality of fingers extending backwards from the first portion for fitting behind the barb of the connector, the fingers having inward extensions at their distal ends, the fingers being adapted for the inward extensions to pass over the barb at the second outer diameter and to move inward for engaging the tube where its diameter reduces from the second outer diameter to the first outer diameter behind the barb;
      a sleeve, movable with respect to the collet, and sized to engage over the collet to urge the fingers of the collet inward for the inward extensions to abut the tube behind the barb and limit movement of the collet forwards along the tube, when the collet and sleeve are secured together in relative position by a means for securing the collet and sleeve together in relative position; and
      the sleeve having a bore sized to receive the tube at its third outer diameter, for urging the tube against the distal end of the barb when the sleeve is secured to the collet in use with the inward extensions of the fingers abutting the tube and limiting forwards movement of the collet, whereby the sleeve having the bore abutting the tube urging it against the distal end of the barb for avoiding an ingress of a fluid between the tube and the distal end of the barb.

2. The retaining clamp assembly as claimed in claim 1, wherein the bore has a sloped surface.

3. The retaining clamp assembly as claimed in claim 1, wherein the bore has a sloped surface and is provided on a return on the sleeve, the return having a first portion extending radially inward orthogonally from the sleeve, and a second portion extending orthogonally from the first portion towards the barb, a distal end of the return defining the sloped surface which cooperates with the tube.

4. The retaining clamp assembly as claimed in claim 1, wherein the means for securing the collet and sleeve together comprising:
   a plurality of projections on an outside surface of each one of the plurality of fingers on the collet;
   a hook on the sleeve constructed to hold a position determined by one of the plurality of projections to secure the collet and sleeve together.

5. The retaining clamp assembly as claimed in claim 4, wherein the hook is on the collet with the plurality of projections on the sleeve.

6. The retaining clamp assembly as claimed in claim 1, wherein four or more fingers are provided on the collet.

7. The retaining clamp assembly as claimed in claim 1, wherein the collet and the sleeve are held together prior to use by at least one frangible connection.

8. The retaining clamp assembly as claimed in claim 1, wherein the clamp is made from plastics material.

9. The retaining clamp assembly as claimed in claim 8, wherein the clamp is made from polypropylene.

10. A retaining clamp assembly comprising:
    a tube;
    a connector; and
    a retaining clamp for retaining the tube on the connector, wherein the connector comprises:
    a spigot; and
    a barb on the spigot, the barb having:
       a barb major dimension having a diameter greater than that of the spigot; and a reduced diameter distal end at a leading end of the spigot;

the tube where retained on the connector having:

a first outer diameter at the spigot behind the barb substantially equal to a diameter of the spigot plus twice a wall thickness of the tube;

a second outer diameter at the barb substantially equal to the diameter of the barb major dimension of the barb plus twice the wall thickness of the tube; and a third outer diameter at the reduced diameter distal end of the barb substantially equal to a diameter of the reduced diameter distal end of the barb plus twice the wall thickness of the tube;

the clamp comprising:

a collet, the collet including a first portion sized to fit over the tube on the barbed connector, and a plurality of fingers extending backwards from the first portion for fitting behind the barb of the connector, the fingers having inward extensions at their distal ends, the fingers being adapted for the inward extensions to pass over the barb at the second outer diameter and to move inward for engaging the tube where its diameter reduces from the second outer diameter to the first outer diameter behind the barb;

a sleeve, movable with respect to the collet, and sized to engage over the collet to urge the fingers of the collet inward for the inward extensions to abut the tube behind the barb and limit movement of the collet forwards along the tube, when the collet and sleeve are secured together in relative position by a means for securing the collet and sleeve together in relative position; and the collet having a bore sized to receive the tube at its third outer diameter, for urging the tube against the distal end of the barb when the sleeve is secured to the collet in use with the inward extensions of the fingers abutting the tube and limiting forwards movement of the collet, whereby the collet having the bore abutting the tube urging it against the distal end of the barb for avoiding an ingress of a fluid between the tube and the distal end of the barb.

11. The retaining clamp assembly as claimed in claim 10, wherein the bore has a sloped surface.

12. The retaining clamp assembly as claimed in claim 10, wherein the bore has a sloped surface formed by a return on the collet, the return extending radially inward orthogonally from the collet, a distal end of the return defining the sloped surface to which cooperates with the tube.

13. The retaining clamp assembly as claimed in claim 10, wherein the means for securing the collet and sleeve together comprising:

a plurality of projections on an outside surface of each one of the plurality of fingers on the collet;

a hook on the sleeve constructed to hold a position determined by one of the plurality of projections to secure the collet and sleeve together.

14. A retaining clamp assembly comprising:

a tube;

a connector; and a clamp for retaining the tube on the connector;

wherein the connector comprises:

a spigot; and a barb on the spigot, the barb having:

a barb major dimension having a diameter greater than that of the spigot; and a reduced diameter distal end at a leading end of the spigot;

the tube where retained on the connector having:

a first outer diameter at the spigot behind the barb substantially equal to a diameter of the spigot plus twice a wall thickness of the tube;

a second outer diameter at the barb substantially equal to the diameter of the barb major dimension of the barb plus twice the wall thickness of the tube; and a third outer diameter at the reduced diameter distal end of the barb substantially equal to a diameter of the reduced diameter distal end of the barb plus twice the wall thickness of the tube;

the clamp comprising:

a collet, the collet including a first portion sized to fit over the tube on the barbed connector, and a plurality of fingers extending backwards from the first portion for fitting behind the barb of the connector, the fingers having inward extensions at their distal ends, the fingers being adapted for the inward extensions to pass over the barb at the second outer diameter and to move inward for engaging the tube where its diameter reduces from the second outer diameter to the first outer diameter behind the barb;

a sleeve, movable with respect to the collet, and sized to engage the collet to urge the fingers of the collet inward for the inward extensions to abut the tube behind the barb and limit movement of the collet forwards along the tube, when the collet and sleeve are secured together in relative position by a means for securing the collet and sleeve together in relative position; and one of the sleeve or the collet having a bore sized to receive the sleeve at its third outer diameter, for urging the tube against the distal end of the barb when the sleeve is secured to the collet in use with the inward extensions of the fingers abutting the tube and limiting forwards movement of the collet, whereby the one of the sleeve or the collet having the bore abuts the tube urging the tube against the distal end of the barb for avoiding ingress between the tube and the distal end of the barb.

* * * * *